United States Patent
Hikichi et al.

(10) Patent No.: US 12,195,592 B2
(45) Date of Patent: Jan. 14, 2025

(54) BISIMIDE PHENOL COMPOUND

(71) Applicant: MITSUBISHI GAS CHEMICAL COMPANY, INC., Tokyo (JP)

(72) Inventors: Tatsuya Hikichi, Tokyo (JP); Daiki Wakahara, Tokyo (JP); Nobuyoshi Ohnishi, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 18/504,785

(22) Filed: Nov. 8, 2023

(65) Prior Publication Data
US 2024/0092975 A1    Mar. 21, 2024

Related U.S. Application Data

(62) Division of application No. 18/025,997, filed as application No. PCT/JP2022/009634 on Mar. 7, 2022, now abandoned.

(30) Foreign Application Priority Data

Apr. 9, 2021  (JP) .................. 2021-066665

(51) Int. Cl.
  *C08G 73/16*  (2006.01)
  *C07D 487/04*  (2006.01)
  *C08G 73/10*  (2006.01)

(52) U.S. Cl.
  CPC ........... *C08G 73/16* (2013.01); *C07D 487/04* (2013.01); *C08G 73/10* (2013.01); *C08G 73/1075* (2013.01); *C08G 73/1067* (2013.01)

(58) Field of Classification Search
  None
  See application file for complete search history.

(56) References Cited

U.S. PATENT DOCUMENTS

| 6,096,853 | A | 8/2000 | Amerik et al. |
| 2010/0113689 | A1 | 5/2010 | Naiki et al. |

FOREIGN PATENT DOCUMENTS

| CN | 111592758 A | 8/2020 |
| JP | 2002-533324 A | 10/2002 |
| JP | 2017-202981 A | 11/2017 |
| JP | 2019-128995 A | 8/2019 |
| JP | 2021-24827 A | 2/2021 |

OTHER PUBLICATIONS

ISR for PCT/JP2022/009634, dated May 24, 2022 (w/ translation).
Bruma et al., "Ordered polyesterimides", Revue Roumaine De Chimie, 30(3):239-244 (1985).
Koton et al., "Synthesis and properties of new polybenzimidazole esterimides", Vysokomlekulyarnye Soedineniya, 17(1):18-21 (1975) (cited in ISR).
Zhuang et al., "Polyimides containing aliphatic/alicyclic segments in the main chains", Progress in Polymer Science, vol. 92, May 2019, pp. 35-88.

*Primary Examiner* — Rachel Kahn
(74) *Attorney, Agent, or Firm* — GREENBLUM & BERNSTEIN, P.L.C.

(57) ABSTRACT

A bisimide phenyl ester acid dianhydride represented by the following formula (2):

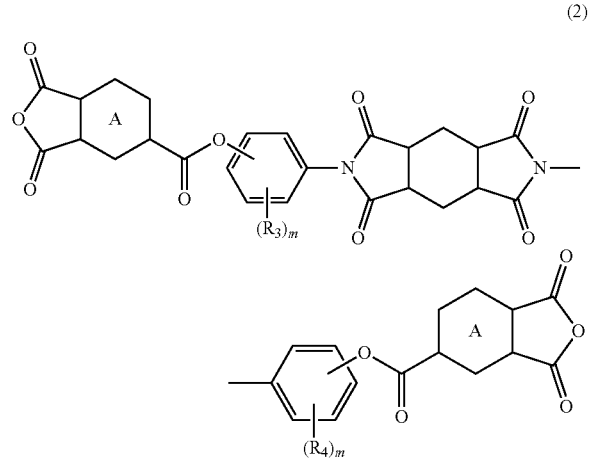

where $R_3$ and $R_4$ each independently represents a hydrogen atom or an organic group having 1 to 10 carbon atoms; each m is independently an integer of 1 to 4; and each A independently represents an aromatic ring or an alicyclic ring.

3 Claims, No Drawings

BISIMIDE PHENOL COMPOUND

CROSS-REFERENCE TO RELATED APPLICATIONS

The is a divisional of U.S. patent application Ser. No. 18/025,997, filed Mar. 13, 2023, which is the U.S. National Stage Entry of PCT/JP2022/009634, filed Mar. 7, 2022, which claims the benefit of JP Appl. No.: 2021-066665, filed Apr. 9, 2021. The content of each application listed above is incorporated herein by reference in its entirety.

TECHNICAL FIELD

The present invention relates to a novel bisimide phenol compound; and a bisimide phenyl ester acid dianhydride, polyamic acid, and polyimide derived from the bisimide phenol compound; and a resin composition containing any of those.

BACKGROUND ART

Because of excellent properties such as mechanical properties, chemical resistance, flame retardancy, and electrical properties in addition to heat resistance, polyimides are widely used in various fields as molding materials, composite materials, and electrical and electronic components.

In recent years, a traction motor has been made smaller in size, lighter in weight, and higher in voltage to extend the cruising range of an electric vehicle. Windings whose conductor surfaces are coated with an insulation coating are used in the traction motor. When an electric current flows through the traction motor, a potential difference is generated between these windings or between the windings and the core. As the voltage of the traction motor increases, this potential difference tends to cause partial discharge. The occurrence of such partial discharge causes damage to the insulation coating, and if the damage progresses, a dielectric breakdown occurs.

In order to prevent such partial discharge, it is considered to increase the thickness of an insulating resin. However, the thicker the insulation coating, the smaller the volume fraction of the conductor. Accordingly, the traction motor may need to increase in size or have high electrical resistance, thus being contrary to compactness and high-power output.

Therefore, Patent Literature 1 discloses that a certain amount of inorganic filler is contained in an insulation coating for the purpose of suppressing erosion due to partial discharge.

CITATION LIST

Patent Literature

Patent Literature 1: Japanese Patent Laid-Open No. 2019-128995

SUMMARY OF INVENTION

Technical Problem

However, since a method described in Patent Literature 1 is to make an insulating resin less susceptible to erosion when partial discharge occurs, the partial discharge will eventually erode the insulating resin and cause a dielectric breakdown. Therefore, as a fundamental solution to the partial discharge associated with smaller size, lighter weight, and higher voltage of a traction motor, it is desired to develop a low dielectric-constant insulation coating material that does not cause partial discharge.

The present invention has been made in view of the above problem, and an object of the present invention is to provide a novel bisimide phenol compound having a low dielectric constant; and a bisimide phenyl ester acid dianhydride, polyamic acid, and polyimide derived from the bisimide phenol compound; and a resin composition containing any of those.

Solution to Problem

The present inventors have conducted intensive studies to achieve the above object. As a result, the present inventors have found that the above object can be achieved by using a novel bisimide phenol compound and polyimide, having a predetermined structure and completed the present invention.

In other words, the present invention is as follows.

[1]

A bisimide phenol compound represented by the following formula (1):

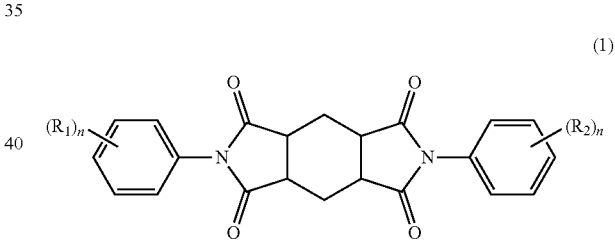

wherein $R_1$ and $R_2$ each independently represent a hydrogen atom, a hydroxy group, or an organic group having 1 to 10 carbon atoms; two or more of both $R_1$ and $R_2$ are hydroxy groups; and each n is independently an integer of 1 to 5.

[2]

The bisimide phenol compound according to [1], wherein one or more of both $R_1$ and $R_2$ are each hydroxy groups.

[3]

A bisimide phenyl ester acid dianhydride represented by the following formula (2):

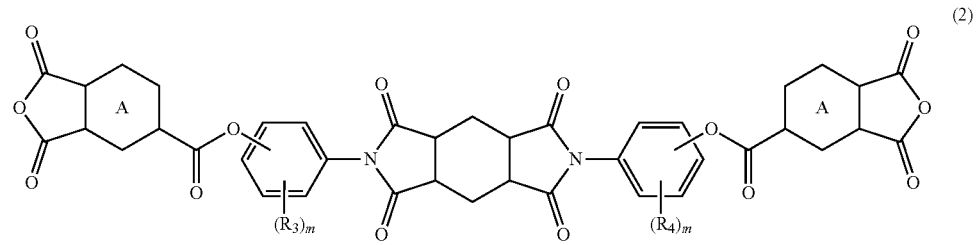

wherein $R_3$ and $R_4$ each independently represent a hydrogen atom or an organic group having 1 to 10 carbon atoms; each m is independently an integer of 1 to 4; and each A independently represents an aromatic ring or an alicyclic ring.

[4]

A polyamic acid having a constituent unit represented by the following formula (3):

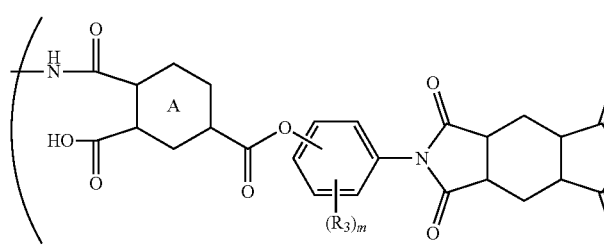

(3)

wherein $R_3$ and $R_4$ each independently represent a hydrogen atom or an organic group having 1 to 10 carbon atoms; each m is independently an integer of 1 to 4; each A independently represents an aromatic ring or an alicyclic ring; and each B independently represents a divalent aromatic group or a divalent aliphatic group.

[5]

The polyamic acid according to [4], wherein a content of a constituent unit derived from bisimide phenyl ester acid dianhydride is 10 mol % to 100 mol % based on the total amount of constituent units derived from acid dianhydrides.

[6]

A polyimide having a constituent unit represented by the following formula (4):

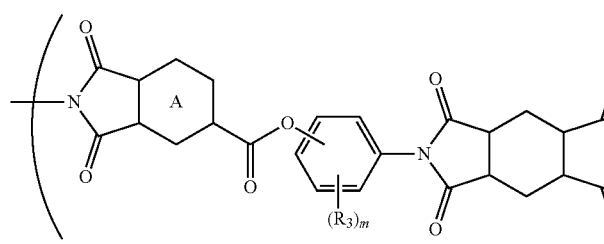

(4)

wherein $R_3$ and $R_4$ each independently represent a hydrogen atom or an organic group having 1 to 10 carbon atoms; each m is independently an integer of 1 to 4; each A independently represents an aromatic ring or an alicyclic ring; and each B independently represents a divalent aromatic group or a divalent aliphatic group.

[7]

The polyimide according to [6], wherein a content of a constituent unit derived from bisimide phenyl ester acid dianhydride is 10 mol % to 100 mol % based on the total amount of constituent units derived from acid dianhydrides.

[8]

A resin composition comprising the bisimide phenol compound according to [1] or [2], the bisimide phenyl ester acid dianhydride according to [3], the polyamic acid according to [4] or [5]; or the polyimide according to [6] or [7].

Advantageous Effect of Invention

The present invention can provide a novel bisimide phenol compound having a low dielectric constant; and a bisimide phenyl ester acid dianhydride, polyamic acid, and polyimide derived from the bisimide phenol compound; and a resin composition containing any of those.

DESCRIPTION OF EMBODIMENTS

Hereinafter, an embodiment of the present invention (hereinafter referred to as "the present embodiment") will be described in detail, but the present invention is not limited thereto. Various modifications can be made without departing from the gist of the present invention.

1. Bisimide phenol compound

The bisimide phenol compound of the present embodiment is represented by the following formula (1):

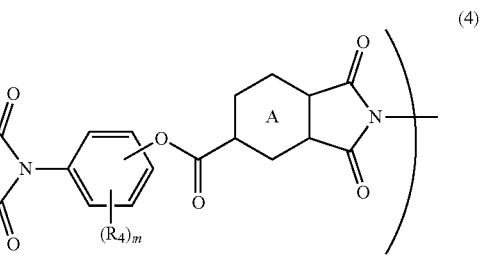

(1)

wherein $R_1$ and $R_2$ each independently represent a hydrogen atom, a hydroxy group, or an organic group having 1 to 10 carbon atoms; two or more of both $R_1$ and $R_2$ are hydroxy groups; and each n is independently an integer of 1 to 5.

Two or more of both $R_1$ and $R_2$ are hydroxy groups, two or more of $R_1$ may be hydroxy groups, two or more of $R_2$ may be hydroxy groups, or one or more of both $R_1$ and $R_2$ may be each hydroxy groups. Among them, $R_1$ and $R_2$ each having one or more hydroxy groups are preferred, and $R_1$ and $R_2$ each having one hydroxy group are more preferred. Thus, when $R_1$ and $R_2$ each have one or more hydroxy groups, a polyamic acid or polyimide obtained by using the bisimide phenol compound has a structure including the above bisimide phenol skeleton in the main chain and tends to have a lower dielectric constant.

In general formula (1), the organic groups having 1 to 10 carbon atoms represented by $R_1$ and $R_2$ are not particularly limited, and examples thereof include alkyl groups such as a methyl group, an ethyl group, an n-propyl group, an isopropyl group, an n-butyl group, an isobutyl group, a sec-butyl group, and a t-butyl group; cycloalkyl groups such as a cyclopropyl group, a cyclobutyl group, a cyclopentyl group, a cyclohexyl group, and a cyclooctyl group; aryl groups such as a phenyl group; aralkyl groups such as a methylphenyl group; and alkenyl groups such as a vinyl group, a propynyl group, and a butynyl group. Among them, alkyl and cycloalkyl groups are preferred. The number of carbon atoms of the organic group is 1 to 10, preferably 1 to 6, and more preferably 1 to 4.

In general formula (1), n indicates the number of substitutions of $R_1$ and $R_2$ for each benzene ring and is 1 to 5, preferably 1 to 3, and more preferably 1 to 2.

A method for producing the bisimide phenol compound of the present embodiment is not particularly limited, and examples thereof include a method of reacting o-, m-, or p-aminophenol with 1,2,4,5-cyclohexanetetracarboxylic dianhydride (HPMDA).

2. Bisimide phenyl ester acid dianhydride

The bisimide phenyl ester acid dianhydride of the present embodiment is represented by the following formula (2):

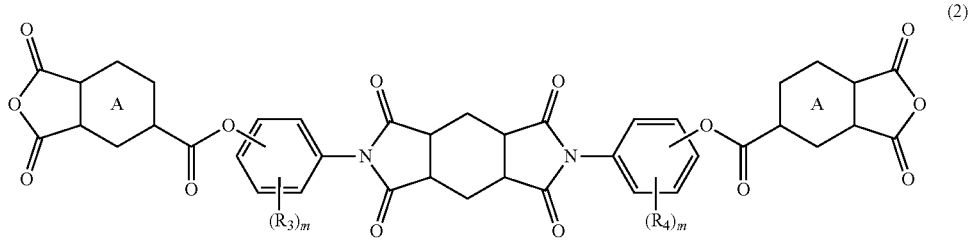

(2)

wherein $R_3$ and $R_4$ each independently represent a hydrogen atom or an organic group having 1 to 10 carbon atoms; each m is independently an integer of 1 to 4; and each A independently represents an aromatic ring or an alicyclic ring.

In general formula (2), the organic groups having 1 to 10 carbon atoms represented by $R_3$ and $R_4$ are not particularly limited, and examples thereof include those similar to the groups exemplified in $R_1$ and $R_2$. m indicates the number of substitutions of $R_3$ and $R_4$ for each benzene ring and is 1 to 4, preferably 1 to 3, and more preferably 1 to 2.

Each A independently represents an aromatic ring or an alicyclic ring, preferably an aromatic ring. Having such a structure, the bisimide phenyl ester acid dianhydride tends to have better heat resistance. Note that the aromatic ring may be a trivalent benzene ring, and the alicyclic ring may be a trivalent cyclohexyl ring.

A method for producing the bisimide phenyl ester acid dianhydride is not particularly limited, and examples thereof include a method of reacting trimellitic anhydride chloride or hydrogenated trimellitic anhydride chloride with the bisimide phenol compound.

3. Polyamic acid

The polyamic acid of the present embodiment has a constituent unit represented by the following formula (3) and may have another constituent unit, if necessary:

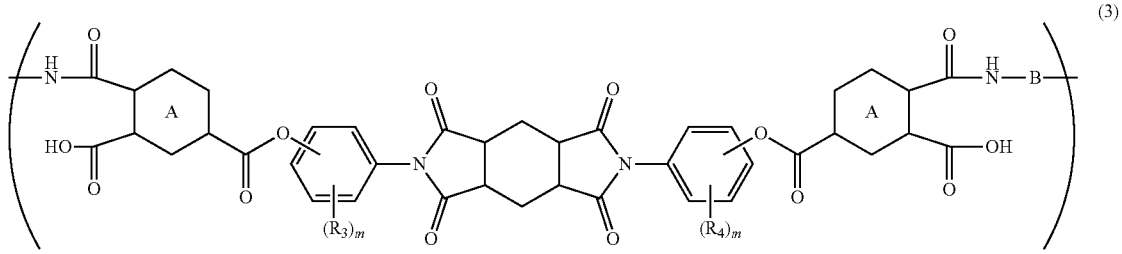

(3)

wherein $R_3$ and $R_4$ each independently represent a hydrogen atom or an organic group having 1 to 10 carbon atoms; each m is independently an integer of 1 to 4; each A independently represents an aromatic ring or an alicyclic ring; and each B independently represents a divalent aromatic group or a divalent aliphatic group.

In general formula (3), the organic groups having 1 to 10 carbon atoms represented by $R_3$ and $R_4$ are not particularly limited, and examples thereof include those similar to the groups exemplified in $R_1$ and $R_2$. In general formula (3), m indicates the number of substitutions of $R_3$ and $R_4$ for each benzene ring and is 1 to 4, preferably 1 to 3, and more preferably 1 to 2.

Each A independently represents an aromatic ring or an alicyclic ring, and is preferably an aromatic ring. Having such a structure, the polyamic acid tends to have better heat resistance. Note that the aromatic ring may be a trivalent benzene ring, and the alicyclic ring may be a trivalent cyclohexyl ring.

Each B independently represents a divalent aromatic group or a divalent aliphatic group. Such divalent aromatic groups are not particularly limited, and examples thereof include divalent monocyclic aromatic groups such as 1,3-phenylene, 1,4-phenylene, 4,4'-biphenylene, 5-chloro-1,3-phenylene, and 5-methoxy-1,3-phenylene; divalent fused-polycyclic aromatic groups such as 1,4-naphthylene, 2,6-naphthylene, 1,4-anthrylene, 9,10-anthrylene, and 3,4-perylenylene; and divalent non-fused polycyclic aromatic groups in which monocyclic aromatic groups such as phenyl and biphenyl, including 2,2-propylidenebis(1,4-phenylene), 2,2-(1,1,1,3,3,3-hexafluoropropylidene)bis(1,4-phenylene), carbonylbis(1,4-phenylene), oxybis(1,4-phenylene), sulfonylbis(1,4-phenylene), and 9,9-fluorenylidenebis(1,4-phenylene) are mutually connected via an oxygen atom, a carbonyl group, an ester group, and a linking group such as methylene, ethylidene, 1-methylethylidene, 1,1-propylidene, 1,4-phenylenebis(1-methylethylidene), 1,3-phenylenebis(1-methylethylidene), cyclohexylidene, phenylmethylene, naphthylmethylene, and 1-phenylethylidene. The aromatic groups may have a substituent such as a methyl group or an ethyl group.

The divalent aliphatic groups are not particularly limited, and examples thereof include divalent linear aliphatic groups such as a methylene group, an ethylene group, a propylene group, a butylene group, a pentylene group, a hexylene group, an octylene group, a decylene group, a dodecylene group, a hexadecylene group, and an octadecylene group; divalent branched aliphatic groups such as an isopropylene group, an isobutylene group, a tertiary butylene group, a neopentylene group, a 2-hexylene group, a 2-octylene group, a 2-decylene group, a 2-dodecylene group, a 2-hexadecylene group, and a 2-octadecylene group; and divalent cyclic aliphatic groups such as a cyclopropylene group, a cyclobutylene group, a cyclopentylene group, a cyclohexylene group, a cyclooctylene group, a cyclodecylene group, a cyclododecylene group, a cyclohexadecylene group, and a cyclooctadecylene group.

The polyamic acid of the present embodiment may be a homopolymer of an amic acid represented by general formula (3) or a copolymer having a constituent unit other than the constituent unit derived from bisimide phenyl ester acid dianhydride as a constituent unit derived from acid dianhydride. In this case, the polyamic acid of the present embodiment may be a block copolymer of a constituent unit of the amic acid represented by general formula (3) and a constituent unit of another amic acid or a random copolymer.

In the polyamic acid of the present embodiment, the constituent unit derived from bisimide phenyl ester acid dianhydride refers to a constituent unit represented by the following formula (3'), excluding the constituent unit (—NH—B—) derived from diamine from general formula (3)

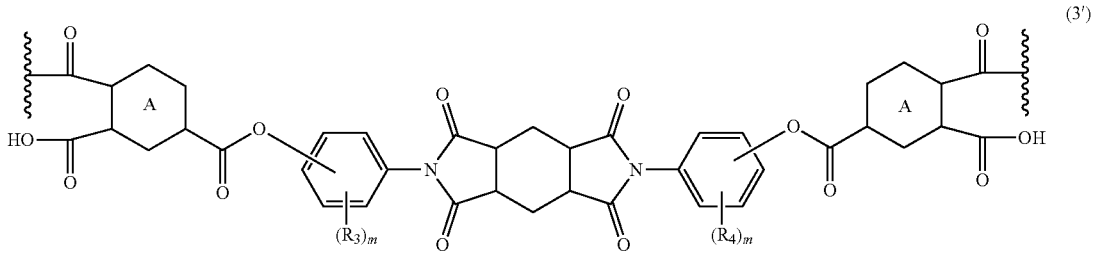

(3')

In the polyamic acid of the present embodiment, the content of the constituent unit derived from bisimide phenyl ester acid dianhydride is preferably 10 to 100 mol %, more preferably 30 to 100 mol %, still more preferably 50 to 100 mol %, further preferably 70 to 100 mol %, even more preferably 80 to 100 mol %, and particularly preferably 90 to 100 mol % based on the total amount of constituent units derived from acid dianhydrides. When the content of the constituent unit derived from bisimide phenyl ester acid dianhydride is within the above range, the polyamic acid tends to have a lower dielectric constant.

Other acid dianhydrides constituting constituent units other than the constituent unit represented by general formula (3) are not particularly limited, and examples thereof include pyromellitic dianhydride, 1,2,3,4-benzenetetracarboxylic dianhydride, 3,3',4,4'-benzophenonetetracarboxylic dianhydride, 2,2',3,3'-benzophenonetetracarboxylic dianhydride, 3,3',4,4'-biphenyltetracarboxylic dianhydride, 2,2',3,3'-biphenyltetracarboxylic dianhydride, 2,3,3',4'-biphenyltetracarboxylic dianhydride, 2,2-bis(3,4-dicarboxyphenyl) propane dianhydride, 2,2-bis(2,3-dicarboxyphenyl) propane dianhydride, bis(3,4-dicarboxyphenyl) ether dianhydride, bis(2,3-dicarboxyphenyl) ether dianhydride, bis(3,4-dicarboxyphenyl)sulfone dianhydride, bis(2,3-dicarboxyphenyl)sulfone dianhydride, 2,3-bis(3,4-dicarboxyphenyl)-1,1,1,3,3,3-hexafluoropropane dianhydride, 2,2-bis(2,3-dicarboxyphenyl)-1,1,1,3,3,3-hexafluoropropane dianhydride, 9,9-bis(4-(3,4-dicarboxyphenoxy)phenyl)fluorene dianhydride, 9,9-bis(4-(2,3-dicarboxyphenoxy)phenyl)fluorene dianhydride, 2,3,6,7-naphthalenetetracarboxylic dianhydride, 1,4,5,8- naphthalenetetracarboxylic dianhydride, and 3,4,9,10-perylenetetracarboxylic dianhydride.

The polyamic acid of the present embodiment preferably has a weight average molecular weight of 3000 to 150000, more preferably 3500 to 100000, and still more preferably 3500 to 75000.

A method for producing the polyamic acid of the present embodiment is not particularly limited, and examples thereof include a polycondensation method of the bisimide phenyl ester acid dianhydride with diamines. In this process, the other acid dianhydrides may be used in combination as necessary. The diamines may be used alone or in combination of two or more.

Examples of the diamines include diamines having a divalent aromatic group or a divalent aliphatic group in B above. Such diamines are not particularly limited, and examples thereof include p-phenylenediamine, m-phenylenediamine, 3,4'-diaminodiphenyl ether, 4,4'-diaminodiphenyl ether, 1,5-naphthylenediamine, 4,4'-diaminodiphenylmethane, 3,4'-diaminodiphenyl sulfone, 4,4'-diaminodiphenyl sulfone, 2,4-diaminochlorobenzene, 2,2-bis[4-(4-aminophenoxy)phenyl]propane, 2,2-[4-(4-aminophenoxyphenyl)][4-(3-aminophenoxyphenyl)]propane, 2,2-bis[3-(3-aminophenoxy)phenyl]-1,1,1,3,3,3-hexafluoropropane, 2,2-bis[4-(4-aminophenoxy)phenyl]-1,1,1,3,3,3-hexafluoropropane, 2,2-[4-(4-aminophenoxyphenyl)][4-(3-aminophenoxyphenyl)]-1,1,1,3,3,3-hexafluoropropane, 1,3-bis(3-aminophenoxy)benzene, 1,4-bis(3-aminophenoxy)benzene, 1,4-bis(4-aminophenoxy)benzene, 1,3-bis(4-aminophenoxy)benzene, and 4,4'-bis(4-aminophenoxy)biphenyl.

Polycondensation of a diamine with acid dianhydride can be carried out in an organic solvent. The organic solvent used in the polycondensation is not particularly limited, and examples thereof may include N,N-dimethylformamide, N,N-dimethylacetamide, N,N-dimethylmethoxyacetamide, N,N-diethylmethoxyacetamide, N-methyl-2-pyrrolidone, N-methylcaprolactam, 1,2-dimethoxyethane, diethylene glycol dimethyl ether, diethylene glycol ethyl methyl ether, diethylene glycol diethyl ether, tetrahydrofuran, 1,3-dioxane, 1,4-dioxane, pyridine, picoline, dimethyl sulfoxide, dimethyl sulfone, and tetramethylurea. These organic solvents may be used alone or in a mixture of two or more.

4. Polyimide

The polyimide of the present embodiment has a constituent unit represented by the following formula (4):

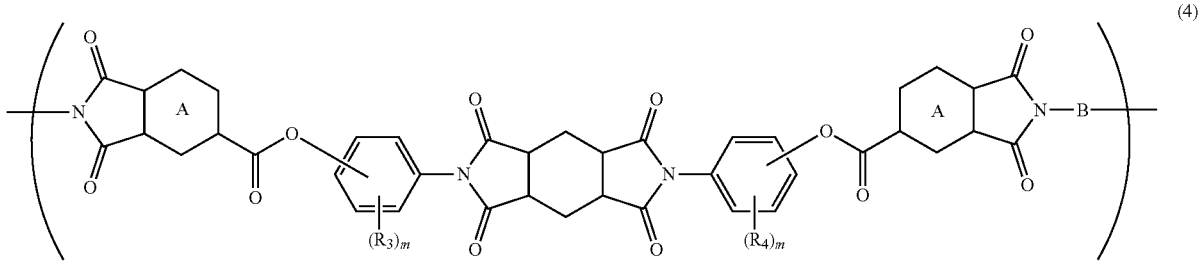

(4)

wherein $R_3$ and $R_4$ each independently represent a hydrogen atom or an organic group having 1 to 10 carbon atoms; each m is independently an integer of 1 to 4; each A independently represents an aromatic ring or an alicyclic ring; and each B independently represents a divalent aromatic group or a divalent aliphatic group.

In general formula (4), the organic groups having 1 to 10 carbon atoms represented by $R_3$ and $R_4$ are not particularly limited, and examples thereof include those similar to the groups exemplified in $R_1$ and $R_2$. In the formula (4), m indicates the number of substitutions of $R_3$ and $R_4$ for each benzene ring and is 1 to 4, preferably 1 to 3, and more preferably 1 to 2.

Furthermore, in general formula (4), A and B are not particularly limited, and examples thereof include those similar to the groups exemplified in general formula (3).

The polyimide of the present embodiment may be a homopolymer of the polyimide represented by general formula (4) or a copolymer having a constituent unit other than the constituent unit derived from bisimide phenyl ester acid dianhydride as a constituent unit derived from acid dianhydride. In this case, the polyimide may be a block copolymer of a constituent unit of the polyimide represented by general formula (4) and a constituent unit of another polyimide or a random copolymer.

In the polyimide of the present embodiment, the constituent unit derived from bisimide phenyl ester acid dianhydride refers to a constituent unit represented by the following formula (4'), excluding the constituent unit (—N—B—) derived from diamine from general formula (4).

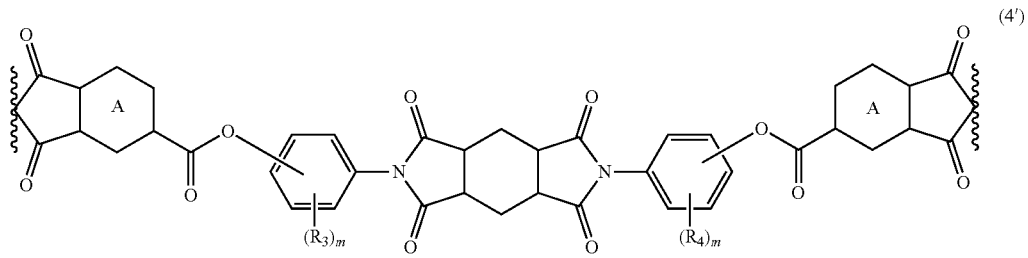

In the polyimide of the present embodiment, the content of the constituent unit derived from bisimide phenyl ester acid dianhydride is preferably 10 to 100 mol %, more preferably 30 to 100 mol %, still more preferably 50 to 100 mol %, further preferably 70 to 100 mol %, even more preferably 80 to 100 mol %, and particularly preferably 90 to 100 mol % based on the total amount of constituent units derived from acid dianhydrides. When the content of the constituent unit derived from bisimide phenyl ester acid dianhydride is within the above range, the polyimide tends to have a lower dielectric constant.

A method for producing the polyimide of the present embodiment is not particularly limited, and examples thereof include a method of imidizing the polyamic acid by cyclodehydration.

Examples of the imidization methods include thermal imidization methods and chemical imidization methods. Examples of thermal imidization methods include a method (a) in which a polyamic acid solution is cast on a smooth surface substrate such as glass or metal and then heated for cyclodehydration and a method (b) in which a polyamic acid solution is directly heated for cyclodehydration. Examples of solvents for the polyamic acid solution in these methods include organic solvents similar to those used in the production of polyamic acid.

In the thermal imidization method (a), a film polyimide can be obtained by heating a thin film formed by casting a polyamic acid solution on a substrate under normal or reduced pressure. In this case, the heating temperature for cyclodehydration is usually 100 to 400° C., preferably 150 to 350° C., and it is preferable to gradually raise the temperature during the reaction.

In the thermal imidization method (b), the polyimide is obtained as a powder or solution by heating the polyamic acid solution. In this case, the heating temperature for cyclodehydration is usually 80 to 300° C., preferably 100 to 250° C.

In the thermal imidization method (b), in order to facilitate the removal of by-product water, it is also possible to allow the presence of components that are azeotropic with water and particularly easily separated from water outside the reaction system, for example, aromatic hydrocarbons such as benzene, toluene, and xylene as dehydrating agents. In the thermal imidization method (b), furthermore, catalysts such as tertiary amines, for example, aliphatic tertiary amines such as trimethylamine, triethylamine, tri-n-propylamine, tri-i-propylamine, and tri-n-butylamine; aromatic tertiary amines such as N,N-dimethylaniline and N,N-diethylaniline; and heterocyclic tertiary amines such as pyridine, quinoline, and isoquinoline may be used to promote cyclodehydration.

Examples of the chemical imidization methods include a method (c) of polyimidization in a solution state using cyclization agents that dehydrate and cyclize polyamic acid, whereby the polyimide can be obtained as a powder or solution.

Examples of the solvents used in this method include organic solvents similar to those used in the production of polyamic acid. The cyclization agents used in the chemical imidization method (c) are not particularly limited, and examples thereof include acid anhydrides such as acetic anhydride, propionic anhydride, and butyric anhydride. These cyclization agents may be used alone or in a mixture of two or more.

The reaction temperature in the chemical imidization method (c) is usually 0 to 200° C. Note that in the chemical imidization method, tertiary amines can be used as a catalyst as in the case of the thermal imidization method.

When the polyimide is obtained as a powder by a thermal imidization method or a chemical imidization method, the polyimide powder can be separated and recovered from a medium by an appropriate method such as filtration, spray drying, and steam distillation. The imidization rate of the polyimide of the present embodiment is 50% or more, preferably 90% or more.

5. Resin composition

The resin composition of the present embodiment contains the above bisimide phenol compound, the above bisimide phenyl ester acid dianhydride, the above polyamic acid, or the above polyimide and may also contain other resins and inorganic fillers as necessary.

The resin-molded product of the present embodiment has a low dielectric constant and can thus be suitably used as a coating material for electric wires used, for example, in driving motors, generators, and accessory motors of hybrid or electric vehicles. In addition, the product can also be suitably used as a protective film for high-frequency and/or high-voltage electric wires, or an insulating film for circuit boards.

EXAMPLES

Hereinafter, the present invention will be described in more detail with reference to Examples and Comparative Examples. However, the present invention is not limited at all by the following Examples.

[NMR Measurement]

1H-NMR was measured by dissolving measurement samples in heavy dimethyl sulfoxide (DMSO-d6; deuteration ratio of D99.9%, 0.05 vol % TMS) containing tetramethylsilane as an internal standard. ASCEND TM 500 manufactured by BRUKER Corporation was used as an NMR instrument.

[Dielectric Constant]

The dielectric constant at 10 GHz of polyimide films obtained in Examples 10 to 15 and Comparative Example 1 was measured three times by a cavity resonator perturbation method (Agilent 8722 ES, manufactured by Agilent Technologies, Inc.) to determine the average value.

[Weight Average Molecular Weight]

The weight average molecular weight of polyamic acids obtained in Examples 10 to 15 in terms of polymethyl methacrylate was measured under the following measurement conditions.

(Measurement conditions)

Device: CBM-20A, SIL-10ADvp, LC-10ADvp, DGU-12A, SPD-10Avp, CTO-10Avp, RID-10A, FRC-10A (all manufactured by Shimazu Corporation)

Column: Shodex GPC K-804

Column temperature: 50° C.

Mobile phase: N-methylpyrrolidone (LiBr (30 mM), $H_3PO_4$ (30 mM))

Mobile phase flow rate: 0.7 mL/min

Molecular weight standard: polymethyl methacrylate (Shodex M-75)

Example 1

To a 500 mL three-necked flask, 44.8 g of 1,2,4,5-cyclohexanetetracarboxylic dianhydride (hereinafter abbreviated as "HPMDA"), 48.0 g of o-aminophenol, and 300 mL of acetic acid were added under nitrogen flow, stirred and refluxed at 110° C. for 6 hours, and then allowed to cool to room temperature. The reaction liquid was poured into a 3 L beaker containing 2 L of $H_2O$ to form a white precipitate. Thereafter, the white precipitate thus formed was thoroughly washed with water and filtered through Kiriyama funnel filter paper No. 5C. The filtrate was collected and dried in vacuum at 100° C. overnight to yield 61.97 g of white powder (yield: 76.2%). The structural formula and 1H-NMR results of the resulting compound are shown below.

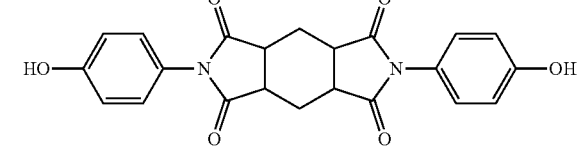

1H-NMR (500 MHz, DMSO-d6):

δ 9.72 (s, 2H), δ 7.28-7.24 (m, 2H), δ 7.10 (br, 2H), δ 6.95-6.93 (d, 2H), δ 6.88-6.87 (t, 2H), δ 3.26-3.20 (m, 4H), δ 2.28 (s, 2H), δ 1.87-1.73 (br, 2H)

Example 2

To a 500 mL three-necked flask, 44.8 g of HPMDA, 48.0 g of m-aminophenol, and 300 mL of acetic acid were added under nitrogen flow, stirred and refluxed at 110° C. for 6 hours, and then allowed to cool to room temperature. The reaction liquid was poured into a 3 L beaker containing 2 L of $H_2O$ to form a white precipitate. Thereafter, the white precipitate thus formed was thoroughly washed with water and filtered through Kiriyama funnel filter paper No. 5C. The filtrate was collected and dried in vacuum at 100° C. overnight to yield 72.2 g of white powder (yield: 88.0%). The structural formula and 1H-NMR results of the resulting compound are shown below.

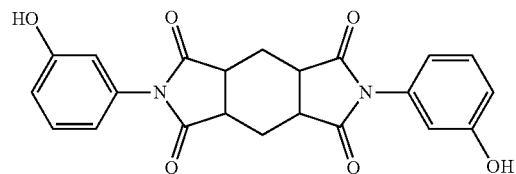

1H-NMR (500 MHz, DMSO-d6):

δ 9.69 (s, 2H), δ 7.26-7.22 (t, 2H), δ 6.80-6.78 (m, 2H), δ 6.68-6.65 (m, 4H), δ 3.18-3.15 (m, 4H), δ 2.36-2.23 (m, 2H), δ 1.95-1.88 (m, 2H)

Example 3

To a 500 mL three-necked flask, 44.8 g of HPMDA, 48.0 g of p-aminophenol, and 300 mL of acetic acid were added under nitrogen flow, stirred and refluxed at 110° C. for 6 hours, and then allowed to cool to room temperature. The reaction liquid was poured into a 3 L beaker containing 2 L of $H_2O$ to form a white precipitate. Thereafter, the white precipitate thus formed was thoroughly washed with water and filtered through Kiriyama funnel filter paper No. 5C. The filtrate was collected and dried in vacuum at 100° C. overnight to yield 76.8 g of white powder (yield: 94.5%). The structural formula and 1H-NMR results of the resulting compound are shown below.

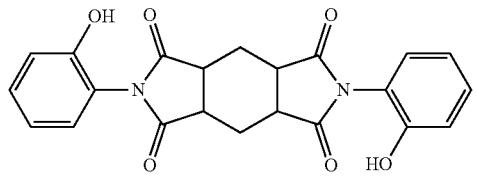 [SMILES: O=C1C2CC3C(=O)N(c4ccccc4O)C(=O)C3CC2C(=O)N1c1ccccc1O]

1H-NMR (500 MHz, DMSO-d6):

δ 9.70 (s, 2H), δ 7.01-6.99 (m, 4H), δ 6.81-6.79 (m, 4H), δ 3.18 (m, 4H), δ 2.37-2.36 (m, 2H), δ 1.95-1.88 (m, 2H)

Example 4

To a 300 mL three-necked flask, 15.0 g of bisimide phenol obtained in Example 1, 60 mL of THF (super dehydrated, stabilizer free), and 9.0 g of pyridine were added under nitrogen flow and stirred for 30 minutes (Container A). In a 100 mL recovery flask, 17.6 g of trimellitic anhydride chloride and 20 mL of THF (super dehydrated, stabilizer free) were dissolved under nitrogen flow (Container B). The solution in Container B was slowly added dropwise to Container A in an ice bath. After being stirred in an ice bath for 2 hours, the mixture was allowed to react at room temperature for 22 hours to form a white precipitate. The white precipitate was taken out from the three-necked flask and thoroughly washed with water with Kiriyama funnel filter paper No. 5C to remove excess amounts of pyridine and pyridine hydrochloride. After being thoroughly washed with water, the product was dried in vacuum at 60° C. The white powder after vacuum drying was stirred in 100 mL of acetic anhydride at 90° C. for 2 hours, thereby being cyclized. Subsequently, toluene was added to the acetic anhydride solution, and the solvents were distilled off with an evaporator to obtain a white powder. The entire white powder obtained was stirred in 100 mL of acetonitrile at 100° C. for 1 hour and thermally filtered. The filtrate was replaced with diethyl ether and dried in vacuum at 100° C. to yield 15.8 g of white powder (yield: 56.7%). The structural formula and 1H-NMR results of the resulting compound are shown below.

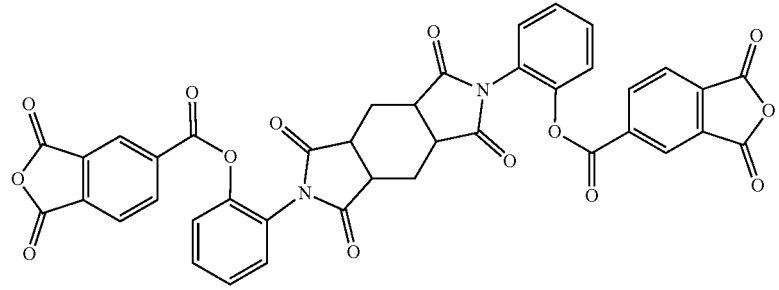 [SMILES: O=C(Oc1ccccc1N1C(=O)C2CC3C(=O)N(c4ccccc4OC(=O)c4ccc5c(c4)C(=O)OC5=O)C(=O)C3CC2C1=O)c1ccc2c(c1)C(=O)OC2=O]

1H-NMR (500 MHz, DMSO-d6):
δ 8.58-8.39 (m, 4H), δ 8.26-8.09 (m, 2H), δ 7.62-7.32 (m, 8H), δ 3.11-3.04 (m, 4H), δ 2.22-1.37 (m, 4H)

Example 5

To a 300 mL three-necked flask, 15.0 g of bisimide phenol obtained in Example 2, 40 mL of THF (super dehydrated, stabilizer free), and 9.0 g of pyridine were added under nitrogen flow and stirred for 30 minutes (Container A). In a 100 mL recovery flask, 17.6 g of trimellitic anhydride chloride and 20 mL of THF (super dehydrated, stabilizer free) were dissolved under nitrogen flow (Container B). The solution in Container B was slowly added dropwise to Container A in an ice bath. After being stirred in an ice bath for 2 hours, the mixture was allowed to react at room temperature for 22 hours to form a white precipitate. The white precipitate was taken out from the three-necked flask and thoroughly washed with water with Kiriyama funnel filter paper No. 5C to remove excess amounts of pyridine and pyridine hydrochloride. After being thoroughly washed with water, the product was dried in vacuum at 60° C. The white powder after vacuum drying was stirred in 100 mL of acetic anhydride at 90° C. for 2 hours, thereby being cyclized. Subsequently, toluene was added to the acetic anhydride solution, and the solvents were distilled off with an evaporator to obtain a white powder. The entire white powder obtained was stirred in 100 mL of acetonitrile at 100° C. for 1 hour and thermally filtered. The filtrate was replaced with diethyl ether and dried in vacuum at 100° C. overnight to yield 8.4 g of white powder (yield: 30.0%). The structural formula and 1H-NMR results of the resulting compound are shown below.

1H-NMR (500 MHz, DMSO-d6):
δ 8.63-8.59 (m, 4H), δ 8.29-8.27 (m, 2H), δ 7.60-7.58 (m, 2H), δ 7.46-7.45 (m, 2H), δ 7.31-7.24 (m, 4H), δ 3.27-3.23 (m, 4H), δ 2.42-2.26 (m, 2H), δ 2.03-1.99 (m, 2H)

Example 6

To a 300 mL three-necked flask, 15.0 g of bisimide phenol obtained in Example 3, 40 mL of THF (super dehydrated, stabilizer free), and 9.0 g of pyridine were added under nitrogen flow and stirred for 30 minutes (Container A). In a 100 mL recovery flask, 17.6 g of trimellitic anhydride chloride and 20 mL of THF (super dehydrated, stabilizer free) were dissolved under nitrogen flow (Container B). The solution in Container B was slowly added dropwise to Container A in an ice bath. After being stirred in an ice bath for 2 hours, the mixture was allowed to react at room temperature for 22 hours to form a white precipitate. The white precipitate was taken out from the three-necked flask and thoroughly washed with water with Kiriyama funnel filter paper No. 5C to remove excess amounts of pyridine and pyridine hydrochloride. After being thoroughly washed with water, the product was dried in vacuum at 60° C. The white powder after vacuum drying was stirred in 100 mL of acetic anhydride at 90° C. for 2 hours, thereby being cyclized. Subsequently, toluene was added to the acetic anhydride solution, and the solvents were distilled off with an evaporator to obtain a white powder. The entire white powder obtained was stirred in 100 mL of acetonitrile at 100° C. for 1 hour and thermally filtered. The filtrate was replaced with diethyl ether and dried in vacuum at 100° C. to yield 13.7 g of white powder (yield: 49.3%). The structural formula and 1H-NMR results of the resulting compound are shown below.

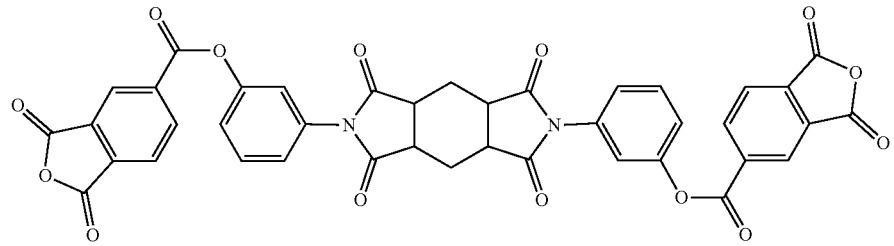 [SMILES: O=C(Oc1cccc(N2C(=O)C3CC4C(=O)N(c5cccc(OC(=O)c6ccc7c(c6)C(=O)OC7=O)c5)C(=O)C4CC3C2=O)c1)c1ccc2c(c1)C(=O)OC2=O]

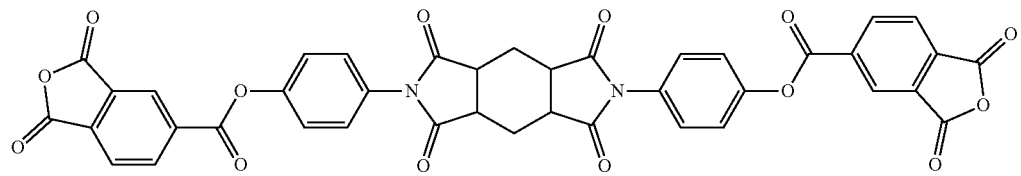 [SMILES: O=C(Oc1ccc(N2C(=O)C3CC4C(=O)N(c5ccc(OC(=O)c6ccc7c(c6)C(=O)OC7=O)cc5)C(=O)C4CC3C2=O)cc1)c1ccc2c(c1)C(=O)OC2=O]

1H-NMR (500 MHz, DMSO-d6):
δ 8.64-8.59 (m, 4H), δ 8.28-8.27 (m, 2H), δ 7.49-7.47 (m, 4H), δ 7.38-7.36 (m, 4H), δ 3.28-3.26 (m, 4H), δ 2.34-2.04 (m, 4H)

Example 7

To a 300 mL three-necked flask, 15.0 g of bisimide phenol obtained in Example 1, 40 mL of THF (super dehydrated, stabilizer free), and 9.0 g of pyridine were added under nitrogen flow and stirred for 30 minutes (Container A). In a 100 mL recovery flask, 18.1 g of hydrogenated trimellitic anhydride chloride and 30 mL of THF (super dehydrated, stabilizer free) were dissolved under nitrogen flow (Container B). The solution in Container B was slowly added dropwise to Container A in an ice bath. After being stirred in an ice bath for 2 hours, the mixture was allowed to react at room temperature for 22 hours to form a white precipitate. The white solid was taken out from the three-necked flask and thoroughly washed with water with Kiriyama funnel filter paper No. 5C to remove excess amounts of pyridine and pyridine hydrochloride. After being thoroughly washed with water, the product was dried in vacuum at 60° C. The white powder after vacuum drying was stirred in 50 mL of acetic anhydride at 90° C. for 2 hours, thereby being cyclized. While the acetic anhydride solution was kept at 90° C., 100 mL of 1,4-dioxane was added to the solution to form a white precipitate. The white precipitate thus formed was filtered through Kiriyama funnel filter paper No. 5C, thoroughly washed with diethyl ether, and dried in vacuum at 80° C. to yield 1.37 g of white powder (yield: 4.84%). The structural formula and 1H-NMR results of the resulting compound are shown below.

1H-NMR (500 MHz, DMSO-d6):
δ 7.53-7.49 (m, 2H), δ 7.40-7.24 (m, 6H), δ 3.55-3.53 (m, 2H), δ 3.28-3.25 (m, 6H), δ 2.70-2.67 (m, 2H), δ 2.41-2.22 (m, 4H), δ 2.17-2.14 (m, 2H), δ 2.07-2.01 (m, 2H), δ 1.92-1.72 (br, 4H), δ 1.67-1.59 (m, 2H), δ 1.40-1.38 (m, 2H)

Example 8

To a 300 mL three-necked flask, 15.0 g of bisimide phenol obtained in Example 2, 40 mL of THF (super dehydrated, stabilizer free), and 9.0 g of pyridine were added under nitrogen flow and stirred for 30 minutes (Container A). In a 100 mL recovery flask, 18.1 g of hydrogenated trimellitic anhydride chloride and 30 mL of THF (super dehydrated, stabilizer free) were dissolved under nitrogen flow (Container B). The solution in Container B was slowly added dropwise to Container A in an ice bath. After being stirred in an ice bath for 2 hours, the mixture was allowed to react at room temperature for 22 hours to form a white precipitate. The white solid was taken out from the three-necked flask and thoroughly washed with water with Kiriyama funnel filter paper No. 5C to remove excess amounts of pyridine and pyridine hydrochloride. After being thoroughly washed with water, the product was dried in vacuum at 60° C. The white powder after vacuum drying was stirred in 100 mL of acetic anhydride at 90° C. for 2 hours, thereby being cyclized. The acetic anhydride solution was allowed to cool to room temperature and then added dropwise with stirring to a 1 L beaker containing 500 mL of diethyl ether to form a white precipitate. The white precipitate thus formed was filtered through Kiriyama funnel filter paper No. 5C, thoroughly washed with diethyl ether, and dried in vacuum at 80° C. to yield 13.0 g of white powder (yield: 46.0%). The structural formula and 1H-NMR results of the resulting compound are shown below.

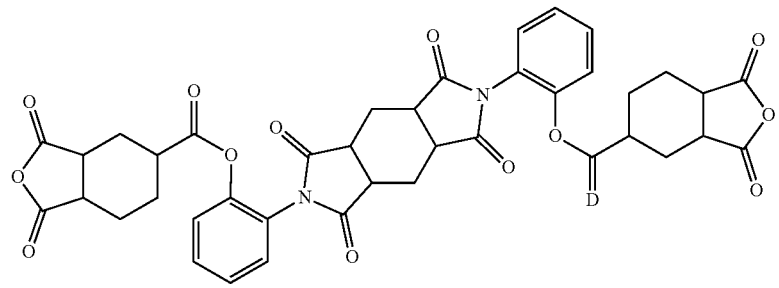

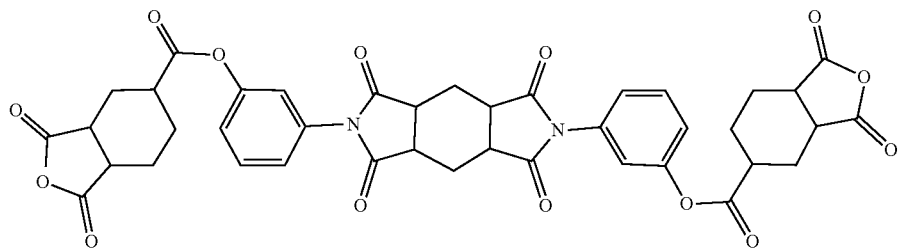 [SMILES: CC(=O)C1CC(C(=O)Oc2cccc(N3C(=O)C4CC5C(=O)N(c6cccc(OC(=O)C7CCC8C(=O)OC(=O)C8C7)c6)C(=O)C5CC4C3=O)c2)CCC1C(=O)O]

1H-NMR (500 MHz, DMSO-d6): δ 7.51-7.49 (m, 2H), δ 7.21-7.14 (m, 4H), δ 7.07-(m, 2H), δ 3.58-3.54 (m, 1H), δ 3.38-3.34 (m, 4H), δ 3.25-3.19 (m, 4H), δ 2.79-2.75 (m, 1H), δ 2.42-1.47 (m, 16H)

Example 9

To a 300 mL three-necked flask, 15.0 g of bisimide phenol obtained in Example 3, 40 mL of THF (super dehydrated, stabilizer free), and 9.0 g of pyridine were added under nitrogen flow and stirred for 30 minutes (Container A). In a 100 mL recovery flask, 18.1 g of hydrogenated trimellitic anhydride chloride and 30 mL of THF (super dehydrated, stabilizer free) were dissolved under nitrogen flow (Container B). The solution in Container B was slowly added dropwise to Container A in an ice bath. After being stirred in an ice bath for 2 hours, the mixture was allowed to react at room temperature for 22 hours to form a white precipitate. The white solid was taken out from the three-necked flask and thoroughly washed with water with Kiriyama funnel filter paper No. 5C to remove excess amounts of pyridine and pyridine hydrochloride. After being thoroughly washed with water, the product was dried in vacuum at 60° C. The white powder after vacuum drying was stirred in 100 mL of acetic anhydride at 90° C. for 2 hours, thereby being cyclized. The acetic anhydride solution was allowed to cool to room temperature and then added dropwise with stirring to a 1 L beaker containing 500 mL of diethyl ether to form a white precipitate. The white precipitate thus formed was filtered through Kiriyama funnel filter paper No. 5C, thoroughly washed with diethyl ether, and dried in vacuum at 80° C. to yield 14.2 g of white powder (yield: 50.0%). The structural formula and 1H-NMR results of the resulting compound are shown below.

N-methylpyrrolidone (hereinafter abbreviated as "NMP") sufficiently dehydrated with molecular sieves 4A were put and dissolved under nitrogen flow. To this solution was added 3.8 g of the acid dianhydride obtained in Example 4 in an ice bath to initiate the polymerization reaction from an initial total solute concentration of 30% by weight. After being stirred for 1 hour with a mechanical stirrer at 150 rpm, the mixture was heated to 50° C. in an aluminum block bath and reacted for 23 hours to obtain a polyamic acid. The obtained polyamic acid had a weight average molecular weight of 39,071. The resulting polyamic acid solution was applied onto a base material, dried at 100° C. for 1 hour, then heated at 200° C. for 1 hour and at 250° C. for 30 minutes, and peeled from the base material to obtain a polyimide film. This polyimide had a dielectric constant of 2.71 at 10 GHz.

Example 11

In a 300 mL separable flask, 1.0 g of ODA and 11.1 g of NMP sufficiently dehydrated with molecular sieves 4A were put and dissolved under nitrogen flow. To this solution was added 3.8 g of the acid dianhydride obtained in Example 5 in an ice bath to initiate the polymerization reaction from an initial total solute concentration of 30% by weight. The mixture was stirred for 24 hours with a mechanical stirrer at 150 rpm to obtain a polyamic acid. The obtained polyamic acid had a weight average molecular weight of 22,291. The resulting polyamic acid solution was applied onto a base material, dried at 100° C. for 1 hour, then heated at 200° C. for 1 hour and at 250° C. for 30 minutes, and peeled from the base material to obtain a polyimide film. This polyimide had a dielectric constant of 2.62 at 10 GHz.

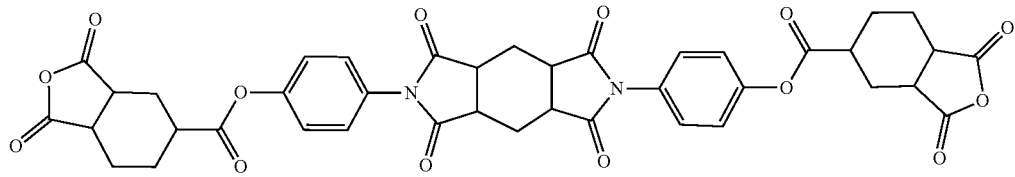 [SMILES: O=C(Oc1ccc(N2C(=O)C3CC4C(=O)N(c5ccc(OC(=O)C6CCC7C(=O)OC(=O)C7C6)cc5)C(=O)C4CC3C2=O)cc1)C1CCC2C(=O)COC(=O)C2C1]

1H-NMR (500 MHz, DMSO-d6):
δ 7.29-7.26 (m, 4H), δ 7.24-7.21 (m, 4H), δ 3.58-3.54 (m, 2H), δ 3.40-3.34 (m, 2H), δ 3.23-3.21 (m, 4H), δ 2.81-2.77 (m, 2H), δ 2.37-2.36 (m, 2H), δ 2.30-2.27 (m, 2H), δ 2.09-2.07 (m, 2H), δ 2.06-1.99 (m, 4H), δ 1.85-1.70 (m, 4H), δ 1.52-1.49 (m, 2H)

Example 10

In a 300 mL separable flask, 1.0 g of 4,4'-diaminodiphenyl ether (hereinafter abbreviated as "ODA") and 11.1 g of Example 12

In a 300 mL separable flask, 1.0 g of ODA and 11.1 g of NMP sufficiently dehydrated with molecular sieves 4A were put and dissolved under nitrogen flow. To this solution was added 3.8 g of the acid dianhydride obtained in Example 6 in an ice bath to initiate the polymerization reaction from an initial total solute concentration of 30% by weight. Four hours after the start of polymerization, 8.0 g of NMP was added thereto. Subsequently, the mixture was stirred for 20 hours with a mechanical stirrer at 200 rpm to obtain a polyamic acid. The obtained polyamic acid had a weight average molecular weight of 67,403. The resulting polyamic acid solution was applied onto a base material, dried at 100° C. for 1 hour, then heated at 200° C. for 1 hour and at 250° C. for 30 minutes, and peeled from the base material to obtain a polyimide film. This polyimide had a dielectric constant of 2.69 at 10 GHz.

Example 13

In a 300 mL separable flask, 0.26 g of ODA and 2.94 g of NMP sufficiently dehydrated with molecular sieves 4A were put and dissolved under nitrogen flow. To this solution was added 1.00 g of the acid dianhydride obtained in Example 7 in an ice bath to initiate the polymerization reaction from an initial total solute concentration of 30% by weight. The mixture was stirred for 48 hours with a mechanical stirrer at 150 rpm to obtain a polyamic acid. The obtained polyamic acid had a weight average molecular weight of 23,312. The resulting polyamic acid solution was applied onto a base material, dried at 100° C. for 1 hour, then heated at 200° C. for 1 hour and at 250° C. for 30 minutes, and peeled from the base material to obtain a polyimide film. This polyimide had a dielectric constant of 2.57 at 10 GHz.

Example 14

In a 300 mL separable flask, 1.0 g of ODA and 11.3 g of NMP sufficiently dehydrated with molecular sieves 4A were put and dissolved under nitrogen flow. To this solution was added 3.8 g of the acid dianhydride obtained in Example 8 in an ice bath to initiate the polymerization reaction from an initial total solute concentration of 30% by weight. The mixture was stirred for 48 hours with a mechanical stirrer at 150 rpm to obtain a polyamic acid. The obtained polyamic acid had a weight average molecular weight of 3,765. The resulting polyamic acid solution was applied onto a base material, dried at 100° C. for 1 hour, then heated at 200° C. for 1 hour and at 250° C. for 30 minutes, and peeled from the base material to obtain a polyimide film. This polyimide had a dielectric constant of 2.70 at 10 GHz.

Example 15

In a 300 mL separable flask, 1.0 g of ODA and 11.3 g of NMP sufficiently dehydrated with molecular sieves 4A were put and dissolved under nitrogen flow. To this solution was added 3.8 g of the acid dianhydride obtained in Example 9 in an ice bath to initiate the polymerization reaction from an initial total solute concentration of 30% by weight. The mixture was stirred for 48 hours with a mechanical stirrer at 150 rpm to obtain a polyamic acid. The obtained polyamic acid had a weight average molecular weight of 13,877. The resulting polyamic acid solution was applied onto a base material, dried at 100° C. for 1 hour, then heated at 200° C. for 1 hour and at 250° C. for 30 minutes, and peeled from the base material to obtain a polyimide film. This polyimide had a dielectric constant of 2.68 at 10 GHz.

Comparative Example 1

In Comparative Example 1, Kapton (R) (manufactured by DU PONT-TORAY CO., LTD.) was used. This polyimide had a dielectric constant of 2.87 at 10 GHz.

TABLE 1

| No. | Structure | Dielectric constant (10 GHz) |
|---|---|---|
| Example 10 | [chemical structure] | 2.71 |
| Example 11 | [chemical structure] | 2.62 |
| Example 12 | [chemical structure] | 2.69 |

TABLE 1-continued

| No. | | Dielectric constant (10 GHz) |
|---|---|---|
| Example 13 | (structure) | 2.57 |
| Example 14 | (structure) | 2.70 |
| Example 15 | (structure) | 2.68 |
| Comparative Example 1 | (structure) | 2.87 |

Moreover, when the glass transition temperatures of Examples 10 and 12 were measured as heat resistance evaluations, the polyimide in Example 10 had a glass transition temperature of 265° C. while the polyimide in Example 12 had a glass transition temperature of 260° C., thus confirming that each had sufficient heat resistance.

Each of the glass transition temperatures was measured using a highly sensitive e-differential scanning calorimeter DSC7020, manufactured by Hitachi High-Tech Corporation. Specifically, the temperature was raised under a nitrogen atmosphere from 30° C. to 350° C. at a heating rate of 10° C./min and then lowered to 30° C. at a cooling rate of 20° C./min. The temperature was further raised repeatedly from 30° C. to 350° C. at a heating rate of 10° C./min, and the glass transition temperature of the polyimide was determined from an inflection point of the second cycle.

INDUSTRIAL APPLICABILITY

In the present invention, a novel bisimide phenol compound as well as a bisimide phenyl ester acid dianhydride, a polyamic acid, and a polyimide derived from the bisimide phenol compound has industrial applicability as coating materials for electric wires used, for example, in traction motors, generators, accessory motors of hybrid or electric vehicles, or as protective films for other high-frequency and/or high-voltage electric wires.

The invention claimed is:

1. A bisimide phenyl ester acid dianhydride represented by the following formula (2):

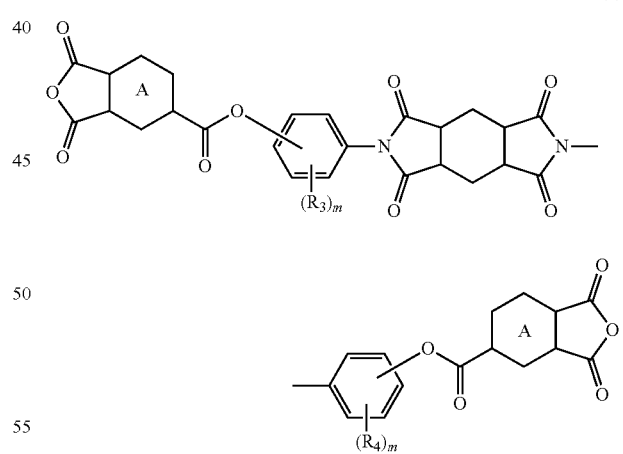

(2)

wherein

R$_3$ and R$_4$ each independently represents a hydrogen atom or an organic group having 1 to 10 carbon atoms;

each m is independently an integer of 1 to 4; and each A independently represents an aromatic ring or an alicyclic ring.

2. A polyamic acid having a constituent unit represented by the following formula (3):

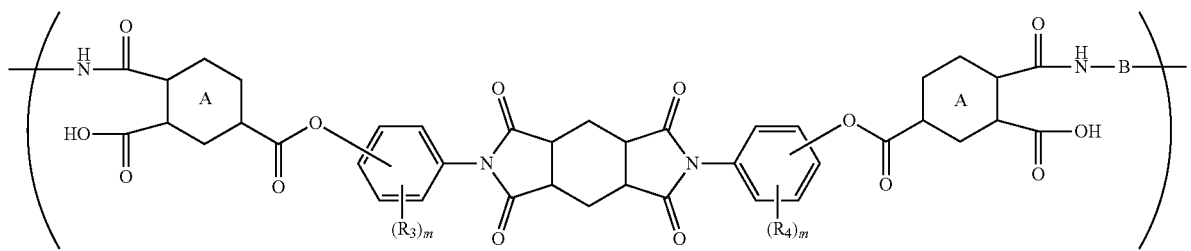

(3)

wherein
R₃ and R₄ each independently represents a hydrogen atom or an organic group having 1 to 10 carbon atoms;
each m is independently an integer of 1 to 4;
each A independently represents an aromatic ring or an alicyclic ring; and
each B independently represents a divalent aromatic group or a divalent aliphatic group.

3. The polyamic acid according to claim 2, wherein a content of a constituent unit derived from bisimide phenyl ester acid dianhydride is 10 mol % to 100 mol % based on the total amount of constituent units derived from acid dianhydrides.

* * * * *